United States Patent [19]

Ridgway

[11] 4,239,622

[45] Dec. 16, 1980

[54] PROCESS FOR THE DISINFECTION OF WATER

[75] Inventor: John W. Ridgway, Tilehurst, England

[73] Assignee: Interox Chemicals Limited, London, England

[21] Appl. No.: 907,018

[22] Filed: May 17, 1978

[30] Foreign Application Priority Data

May 27, 1977 [GB] United Kingdom ............... 22597/77

[51] Int. Cl.³ ............................ C02F 1/50; C02F 1/76
[52] U.S. Cl. .................................... 424/130; 210/754; 422/37; 424/325; 424/149
[58] Field of Search .......................... 210/62, 63 R, 64; 422/28, 37; 424/130, 325

[56] References Cited

U.S. PATENT DOCUMENTS

| | | | |
|---|---|---|---|
| 2,917,428 | 12/1959 | Hitzman | 210/64 |
| 2,944,967 | 7/1960 | Dunklin et al. | 210/64 |
| 3,189,518 | 6/1965 | Glasgow | 210/64 |
| 3,386,915 | 6/1968 | Rutschi et al. | 210/64 |
| 3,454,427 | 7/1969 | Suzum et al. | 210/62 |

FOREIGN PATENT DOCUMENTS 5132057 3/1976 Japan ........................................ 210/62

*Primary Examiner*—Bradley R. Garris
*Attorney, Agent, or Firm*—Larson, Taylor and Hinds

[57] ABSTRACT

A process for disinfecting a water supply, employing as disinfectant a combination of monochloroamine and hydrogen peroxide for use as a disinfectant.

The concentration of monochloroamine is preferably at least 0.02 ppm and generally not more than 0.5 ppm. The concentration of hydrogen peroxide is preferably at least 0.1 ppm and often not more than 1 ppm. Preferably the weight ratio of hydrogen peroxide to monochloroamine is in the range of 4:1 to 20:1.

An advantage of employing a combination of monochloroamine and hydrogen peroxide as disinfectant is that a comparatively long lasting residual bactericide is thereby provided.

4 Claims, 4 Drawing Figures

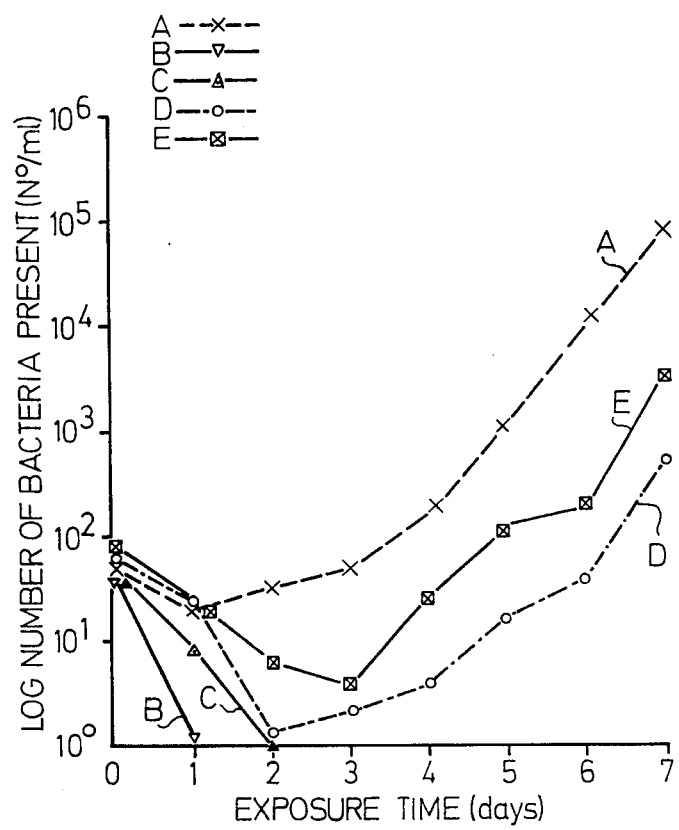

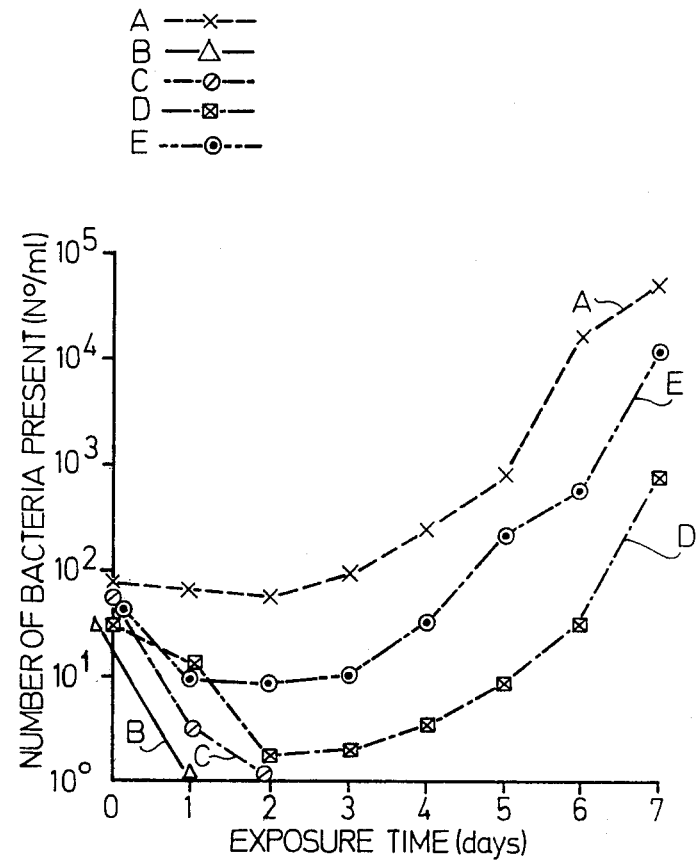

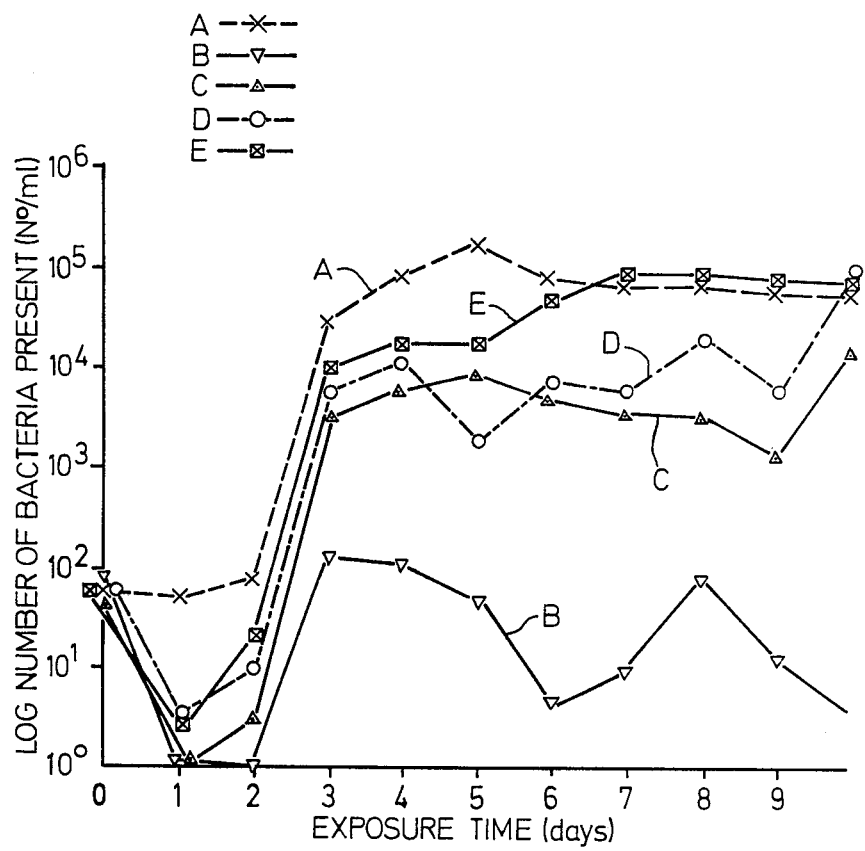

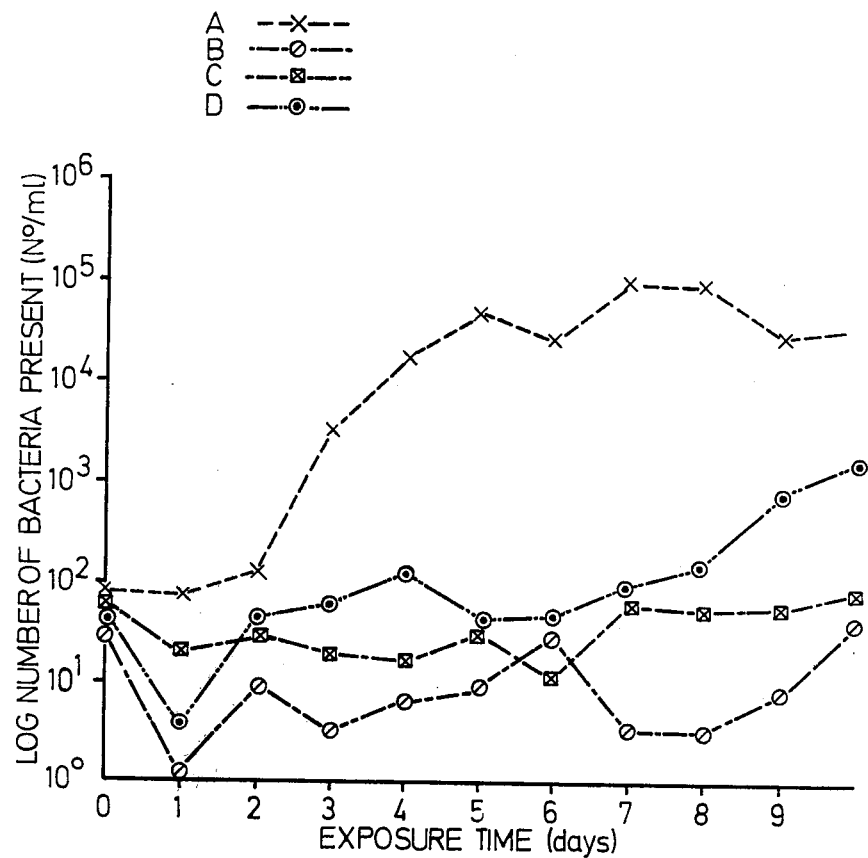

PROCESS FOR THE DISINFECTION OF WATER

The present invention relates to the disinfection of water supplies.

Disinfection of water supplies, and in particular potable water supplies, has been accepted as beneficial for very many years. Efforts in the past have been principally directed to obtaining a 100% kill of pathogens and faecal indicators plus a high level of removal of all other bacteria, but increasing attention is now being paid to the prevention of after growth, that is to say to the proliferation of bacteria in the treated water during its distribution. The problem of after growth can occur for a variety of reasons. First, conventional disinfectant processes can leave a very small proportion of bacteria in the water. Secondly, inadequate monitoring or overload on the treatment plant can lead to less effective disinfection than normal. Thirdly, fresh bacteria can be introduced throughout the distribution system itself, for example by growth on materials of construction or during main laying or repair and from contact with the walls and air in service reservoirs and water storage towers. Occurrence of after growth can lead to malodours or an unpleasant taste in the water supply. Complaints of dirty water may become more accentuated and aquatic life, using bacteria as nutrients, may proliferate. After-growth can also lead to an increase in bacteriologically induced corrosion, or, if there is a build up of bacterial deposits, an increase in pumping costs. The problem of after-growth assumes greater importance when climatic conditions favour proliferation of the bacteria, i.e. hot summer weather, or when residence time in the distribution system is lengthened, or when damage to the system occurs.

Various methods of disinfection are currently employed to a greater or lesser extent. The most important of these is the addition of chlorine, either as free chlorine or combined chlorine or as chlorine dioxide. Although free chlorine is the most effective bactericide, it is so reactive chemically that may retain residuals only briefly in distribution. Furthermore, introduction of chlorine into water supplies containing ammoniacal substances can result under some circumstances in the formation of dichloramine and trichloramine, both of which are distasteful to humans. Other methods of disinfection in use, include the use of ozone and ultra-violet irradiation, but neither of these treatments give rise to any bactericidal residual. Treatment of water supplies with hydrogen peroxide by itself has also been proposed but hydrogen peroxide is a comparatively inefficient bactericide so that in general its use does not represent a practical proposition for this purpose.

We have found that beneficial effects can be obtained by employing a combination of hydrogen peroxide and monochloramine in water supplies.

According to the present invention there is provided a process for disinfecting water supplies with a combination of monochloramine and hydrogen peroxide. There is also provided a composition comprising an aqueous solution of monochloramine and hydrogen peroxide for use as a disinfectant.

Advantageously, we have found that monochloramine and hydrogen peroxide can co-exist for periods of several days when present in water supplies in concentrations sufficient to inhibit bacterial growth. By way of contrast, hydrogen peroxide and free chlorine react together exceedingly quickly, removing the bactericidal properties of each disinfectant.

Desirably, the water supply is treated with at least 0.01 ppm monochloramine, parts per million herein being by weight, unless otherwise stated. Desirably, the water supply contains at least 0.05 ppm hydrogen peroxide. However, although the presence of such characteristics of hydrogen peroxide and monochloramine does effect some control on the bacteria in the water, preferably at least one or other of the two components is present in higher concentration. Thus, the concentration of monochloramine in the water is preferably at least 0.02 ppm, and a preferred concentration of peroxide is at least 0.1 ppm. The effect, in general, of increasing concentrations of one or both of the components is to reduce the survival rate of the bacteria in solution. In some circumstances, the distribution system for water includes covered storage reservoirs (service reservoirs), into which disinfected water is continually being discharged and from which water is constantly being withdrawn. From our tests, it would appear that levels of bacteria in such reservoirs can be controlled by maintaining in the influent water concentrations of at least 0.1 ppm hydrogen peroxide and at least 0.025 ppm monochloramine.

If higher concentrations of peroxide or chloramine are employed, the level of bacteria in the water progressively decreases, so that for example at 0.025 ppm chloramine and 0.5 ppm hydrogen peroxide, a substantially 100% kill of the bacteria can be maintained under the conditions of the test. Of course, higher levels still of hydrogen peroxide or monochloramine could be employed but these would merely serve as a buffer against much greater and unexpected innoculations of bacteria into the system. In practice, the concentration of monochloramine and hydrogen peroxide in the water required to combat the bacteria, is determined by the initial level of bacteria in the water. In general, the concentration of monochloramine will be not more than 0.5 ppm and for many purposes will not be more than 0.1 ppm chloramine. Also, the concentration of hydrogen peroxide in the water will in general be not more than 5 ppm and often not more than 1 ppm.

From the immediately proceeding paragraph, it will be seen that the ratio of chloramine or hydrogen peroxide can be varied over a wide range. Preferably the weight ratio is at least 2:1 for hydrogen peroxide to monochloramine and generally not more than 50:1, and often in the range of 4:1 to 20:1.

The concentration of hydrogen peroxide solution used to treat the water supplies is not critical, and any commercially available concentration can be employed. For convenience, the concentration is preferably between 25% and 70% weight for weight. If desired the hydrogen peroxide solution can be diluted readily to any concentration, for example so as to render the accurate addition of peroxide easier and can contain if desired the monochloramine in an appropriate amount. Monochloramine, for incorporation in the water supplies, directly or in the peroxide solution, can be produced by any known chemical method. Thus, in one method, chlorine is reacted with ammonium chloride in a borax buffer at pH 8.5 and in another, chlorine is reacted with aqueous ammonia at pH 7.5.

If the monochloramine is generated in situ by reaction between chlorine and dissolved ammoniacal substances, preferably sufficient hydrogen peroxide is added thereafter to leave a residual within the range of preferred amounts disclosed hereinbefore, after allowing for the amount that would react with residual free chlorine.

Having described the invention generally, certain embodiments will now be described more fully by way of example.

In the examples, the water used had the following characteristics:

TABLE 1

| Characteristic | Test Water Value |
|---|---|
| Total hardness mg $CaCo_3$/liter | 286 |
| Carbonate hardness as mg $CaCo_3$/liter | 261 |
| Non-carbonate hardness as mg $CaCo_3$/liter | 25 |
| Calcium hardness as mg $CaCo_3$/liter | 277 |
| Magnesium hardness as mg $Mg^{2+}$/liter | 2.0 |
| Iron as mg Fe/liter | 0.01 |
| Copper as mg Cu/liter | 0.03 |
| Nitrate as mg N/liter | 4.0 |
| Ammonia as mg N/liter | 0.02 |
| Total organic Nitrogen mg n/liter | 0.1 |
| Permanganate value mg O/liter | 0.3 |
| Total organic carbon mg C/liter | 0.4 |
| pH | 7.5 |

The water had been drawn directly from the rising main and, except in Example 3B, had been dechlorinated using a HANOVIA fluorescent lamp model 16 with the filter removed.

The bacteria used in the examples was an equal mixture of five cultures produced in the laboratory, namely *Escherichia coli, Streptococcus faecalis* (NCIB 775), *Pseudomonas aeruginosa* (NCIB 8295), Enterobacter sp. and Chromobacterium sp. Laboratory cultures were employed so as to obtain reproducible results and to remove the random element which occurs when natural water samples are employed. The bacterial count was determined by innoculating plates of nutrient agar with 1 ml samples of the water, optionally diluted ten fold in quarter strength Ringer solution. Where it was anticipated that the water would contain relatively small numbers of bacteria, 10 ml samples were used instead. The plates were incubated at 37° C. for 24 hours and then counted.

EXAMPLE 1

In this example the disinfectant effect of a combination of hydrogen peroxide and monochloramine was compared with hydrogen peroxide, with monochloramine, and a control (free of disinfectant). Freshly made solutions containing the appropriate amount of disinfectant were innoculated with bacteria to a level of 50 bacteria per ml, and the level measured daily thereafter.

The initial solution compositions are summarized in Table 2 and the results are summarized in FIGS. 1 and 2, FIG. 1 showing the effectiveness of hydrogen peroxide alone in comparison with a control, and FIG. 2 showing the effectiveness of a combination of hydrogen peroxide and monochloramine in comparison with a control, and monochloramine alone.

TABLE 2

| FIG. No. | Graph | $H_2O_2$ Conc. mg/liter | $NH_2Cl$ Conc. mg/liter |
|---|---|---|---|
| 1 | A | — | — |
| 1 | B | 5 | — |
| 1 | C | 0.5 | — |
| 1 | D | 0.2 | — |
| 1 | E | 0.1 | — |
| 2 | A | — | — |
| 2 | B | 0.5 | 0.025 |

TABLE 2-continued

| FIG. No. | Graph | $H_2O_2$ Conc. mg/liter | $NH_2Cl$ Conc. mg/liter |
|---|---|---|---|
| 2 | C | 0.2 | 0.025 |
| 2 | D | 0.1 | 0.025 |
| 2 | E | 0.025 | — |

It will be self evident from the Figures and Table 2 that the combination performed better than either monochloramine or hydrogen peroxide alone.

EXAMPLE 2

In this example, the effectiveness of a combination of hydrogen peroxide and monochloramine was compared with monochloramine alone, or hydrogen peroxide alone under conditions in which half of the water was discarded daily and replaced by fresh water containing the initial level of bacteria and disinfectants. The bacterial numbers were measured daily. The initial solution compositions are summarised in Table 3 and the results are summarised in FIGS. 3 and 4. The method simulates a service reservoir (or covered storage reservoir) used for short term storage.

TABLE 3

| FIG. No. | Graph | $H_2O_2$ Conc. mg/liter | $NH_2Cl$ Conc. mg/liter |
|---|---|---|---|
| 3 | A | — | — |
| 3 | B | 5.0 | — |
| 3 | C | 0.5 | — |
| 3 | D | 0.2 | — |
| 3 | E | 0.1 | — |
| 4 | A | — | — |
| 4 | B | 0.2 | 0.025 |
| 4 | C | 0.1 | 0.025 |
| 4 | D | 0.025 | — |

From FIGS. 3 and 4 it can be seen that a combination of peroxide and monochloramine was capable of maintaining the bacterial numbers below that of the innoculum, particularly at a concentration of at least 0.2 ppm hydrogen peroxide in combination with 0.025 ppm monochloramine.

EXAMPLE 3

In this example, pipeline distribution was simulated, using a 200 m polyethylene pipe having a diameter of 19 mm, fed from the mains. The water was dosed with bacteria and contained bactericides shown in Table 4 against mains pressure using Metripump Q/5513 pumps, whilst the pipe was delivering 4 liters/minute. Once a steady state had been achieved, the outlet was shut down to maintain the necessary residence time and pumping stopped. Residence times of above 20 hours were obtained only by closing the system down after 20 hours so that contact periods in excess of 20 hours represented 20 hours flowing contact plus the balance in static contact.

The bacterial counts of the water samples and the residual levels of bactericides were measured at time zero, and after 6, 22, and 40 hours, and the results summarized in Tables 4 and 5.

In run B, the water was dechlorinated by addition of sufficient thiosulphate, and runs A and B are present by way of comparison only.

TABLE 4

| Run | Chlorine Residual (ppm) | H$_2$O$_2$ Residual (ppm) | Numbers of Bacteria ml | | | After (hours) |
|---|---|---|---|---|---|---|
| | | | 0 | 6 | 22 | 40 |
| A | 0.1 | — | 90 | 27 | 11 | 0 |
| B | — | 0.25 | 150 | 140 | 16 | 12 |
| C | 0.1 | 0.25 | 87 | 52 | 0 | 0 |

TABLE 5

| Run | | Residual (ppm) | | After (hours) | |
|---|---|---|---|---|---|
| | | 0 | 6 | 22 | 40 |
| A | Free chlorine | 0.04 | 0.04 | 0.02 | <0.02 |
| | Combined chlorine | 0.06 | 0.05 | 0.06 | 0.03 |
| B | H$_2$O$_2$ | 0.25 | 0.20 | <0.1 | <0.1 |
| C | Free chlorine | 0.045 | <0.02 | 0 | 0 |
| | Combined chlorine | 0.05 | 0.045 | 0.05 | 0.035 |
| | H$_2$O$_2$ | 0.2 | 0.15 | <0.1 | <0.1 |

I claim:

1. A process for disinfecting a water supply employing as disinfectant, in combination, 0.025–0.1 ppm monochloroamine and 0.1 to 0.5 ppm hydrogen peroxide in the water supply.

2. A process according to claim 1 wherein the weight ratio of hydrogen peroxide to monochloroamine is at least 2:1.

3. A process according to claim 1 wherein the weight ratio of hydrogen peroxide to monochloroamine is not more than 50:1.

4. A process according to claim 1 wherein the weight ratio of hydrogen peroxide to monochloroamine is in the range of 4:1 to 20:1.

* * * * *